United States Patent [19]

Schnettler et al.

[11] Patent Number: 4,868,197

[45] Date of Patent: Sep. 19, 1989

[54] REDUCING REPERFUSION INJURY WITH 1,3-DIHYDRO-4-METHYL-5-(4-METHYL-THIO)BENZOYL)-2H-IMIDAZOL-2-THIONE

[75] Inventors: Richard A. Schnettler; Richard C. Dage, both of Cincinnati, Ohio; J. Martin Grisar, Wissembourg, France; Frank P. Palopoli, Cincinnati, Ohio

[73] Assignee: Merrell Dow Pharmaceuticals Inc., Cincinnati, Ohio

[21] Appl. No.: 173,037

[22] Filed: Mar. 21, 1988

Related U.S. Application Data

[63] Continuation of Ser. No. 28,525, Mar. 20, 1987, abandoned.

[51] Int. Cl.$^4$ .................. A61K 31/415; C07D 233/70
[52] U.S. Cl. ..................................... 514/392; 548/321
[58] Field of Search ......................... 548/321; 514/392

[56] References Cited

U.S. PATENT DOCUMENTS 4,367,236   1/1983   Grisar et al. .................. 548/321
4,405,635   9/1983   Schnettler et al. ............. 514/392

OTHER PUBLICATIONS

Chemical Abstracts, vol. 90, No. 64361j (1979), abstracting Japanese Patent Appln. No. 78 52, 422, published Oct. 22, 1976, T. Endo, et al., inventors.
Chemical Abstracts, vol. 87, No. 152201a (1977), abstracting Japanese Patent Appln. No. 77 46,074, published Oct. 11, 1975, M. Miyoshi, et al., inventors.
R. C. Smith, J. C. Reeves, R. C. Dage, and R. A. Schnettler, Biochemical Pharmacology 36(9), 1457 (1987).
J. M. McCord, *New Engl. J. Med.* 312, 159 (1985).
Chemical Abstracts, vol. 101, No. 211047 (1984), abstracting S. Maeda, et al., *Chem Pharm. Bull.*, Tokyo 32(7), 2536 (1984).

*Primary Examiner*—Mary C. Lee
*Assistant Examiner*—Zinna Northington
*Attorney, Agent, or Firm*—Michael J. Sayles

[57] ABSTRACT

A sulfur analog of enoximone, 1,3-dihydro-4-methyl-5-[4-(methylthio)benzoyl]-2H-imidazol-2-thione, is reported to reduce reperfusion injury, the injry which occurs when molecular oxygen is reintroduced into an ischemic tissue. The compound could be used to prevent much of the damage which occurs to the heart of a heart attack victim.

1 Claim, No Drawings

REDUCING REPERFUSION INJURY WITH 1,3-DIHYDRO-4-METHYL-5-(4-METHYLTHIO)-BENZOYL)-2H-IMIDAZOL-2-THIONE

This is a continuation of application Ser. No. 028,525, filed Mar. 20, 1987, now abandoned.

FIELD OF THE INVENTION

This invention relates to a pharmaceutical agent which is useful in reducing the damage caused during reperfusion of an ischemic tissue.

BACKGROUND OF THE INVENTION

Heart attack is a leading cause of death. Until recently it was thought that the oxygen deprivation to the heart muscle, cardiac ischemia, was the significant cause of damage to the heart in heart attack victims. While true that lack of oxygen to the heart or a region of the heart will eventually result in cell death, no significant injury occurs to the heart for at least thirty to forty minutes in the absence of molecular oxygen. Recent findings suggest that much of the injury to the heart following an ischemic event of relatively short duration occurs during the reperfusion of the ischemic tissue with oxygenated blood and may be caused by oxygen derived free radicals.

The compound 1,3-dihydro-4-methyl-5-[4-(methylthio)benzoyl]-2H-imidazol-2-one, enoximone, is known to be a cardiotonic agent useful in the treatment of heart failure, for example, congestive heart failure. Enoximone apparently functions by increasing cardiac contractility thereby increasing the pumping ability of the heart. The stronger heart is then better able to supply blood to the organs of the body. While not curing or treating the underlying condition or disease causing the heart failure, enoximone treats the most serious symptom, i.e. lack of adequate blood supply to the tissues and organs of the body. Enoximone may also act to relieve the symptoms of heart failure by acting as a vasodilator, thereby reducing the resistance of blood flow to the body tissues.

1,3-dihydro-4-methyl-5-[4-(methylthio)benzoyl]-2H-imidazol-2-thione, the thio analog of enoximone, the compound of this invention, is generically known from U.S. Pat. No. 4,405,628 and is also generically disclosed to be a cardiotonic agent. Indeed applicants have determined that the thio analog of enoximone has about one-sixth the potency of enoximone in enhancing cardiac contractile strength. Now it has been discovered that the thio analog of enoximone, 1,3-dihydro-4-methyl-5-[4-(methylthio)benzoyl]-2H-imidazol-2-thione, when administered to a patient prior to an ischemic event, during an ischemic event, or during the period of time subsequent to an ischemic event during which reperfusion damage occurs, prevents or lessens the damage which normally occurs when circulation is restored to an ischemic tissue.

SUMMARY OF THE INVENTION

The compound 1,3-dihydro-4-methyl-5-[4-(methylthio)benzoyl-2H-imidazol-2-thione having the structure 1:

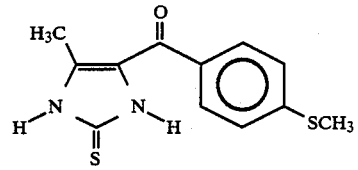

as well as its pharmaceutically acceptable salts is useful in reducing reperfusion injury, i.e. the injury occuring during the reperfusion of an ischemic tissue.

DETAILED DESCRIPTION OF THE INVENTION

The compound of structure 1 is acidic and can form pharmaceutically acceptable salts with suitable inorganic bases. These salts include those of the alkali metals such as lithium, sodium, or potassium. These salts can be prepared using conventional means such as by neutralizing a solution of the free acid in a polar solvent with a stoichiometric quantity of base, for example, an alkoxide such as sodium methoxide or potassium ethoxide or a hydride such as lithium hydride. These reactions are preferably carried out in solution. Suitable solvents are, for example, lower alcohols such as methanol, ethanol, isopropanol, or n-propanol; the ketonic solvents such as acetone or methylethylketone; or dimethylformamide (DMF). Typically about 1 molar equivalent of the free acid compound of structure 1 is allowed to react with about 1 molar equivalent of the base for about 1 minute to about 24 hours, preferably about 1 hour, depending on the reactants and the temperature which can be from about $-30°$ C. to about 78° C., preferably about 0° C. to about 25° C. In general the pharmaceutically acceptable salts are crystalline materials which are more soluble in water and various hydrophilic solvents and which in comparison to the free acid form generally demostrate higher melting points and an increased chemical stability.

The compound of this invention is readily prepared by, for example, the procedure set forth in U.S. Pat. No. 4,405,628. Essentially this procedure requires that the aminodiketone of structure 2:

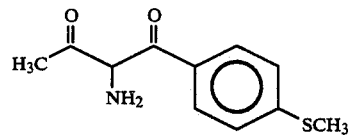

be allowed to react with a thiocyanate salt, preferably sodium or potassium thiocyanate. This reaction is performed by mixing about 1 molar equivalent of the aminodiketone with about 1 to about 5 molar equivalents, preferably about 2 molar equivalents, of the thiocyanate salt in a suitable solvent. The reaction is acid catalyzed and the additional presence of a mild acid, for example, a dilute mineral acid such as dilute hydrochloric acid, sulfuric acid, or phosphoric acid, a carboxylic acid such as acetic acid, trifluoroacetic acid, benzoic acid, or formic acid, or a sulfonic acid such as methanesulfonic acid or p-toluenesulfonic acid, in the reaction mixture is preferred. Preferably the solvent will act as the acid catalyst. The reaction is allowed to proceed for about 5 minutes to about 10 hours depending on, for example, the solvent and the temperature which can be from about 0° C. to about 100° C. Conveniently the reaction can be carried out at room temperature, i.e. about 25° C., and this is preferred. Suitable solvents for this reaction can be any non-reactive solvent such as water or a water miscible solvent, for example, an organic acid such as acetic acid; an alcohol such as methanol or ethanol; or an ether such as tetrahydrofuran or p-dioxan. Preferably any non-aqueous solvent will be mixed with water. The preferred solvent is a mixture of acetic acid and water.

The product of this reaction can be isolated and purified by any suitable art known procedures such as by precipitation of the product or by removal of the reaction solvent by evaporation. The product can successfully be purified by recrystallization from a mixture of ethanol and methanol. Conveniently, when the solvent for this reaction is a mixture of acetic acid and water and potassium thiocyanate is the thiocyanate salt, the product separates from the reaction mixture as a crystalline substance which can then readily be isolated by filtration.

The aminodiketone of structure 2 can be prepared by, for example, reduction of the corresponding oxime of structure 3:

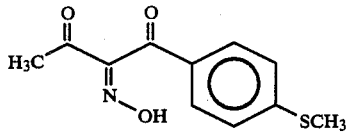

3

Suitable means for reducing the oximes of structure 3 include catalytic reductions employing hydrogen gas and a noble metal catalyst such as Raney nickel, platinum, palladium, rhodium, ruthenium or platinum oxide; and dissolving metal reductions employing lithium, sodium, potassium, calcium, zinc, magnesium, or tin in liquid ammonia or a low-molecular weight aliphatic amine or sodium, aluminum or zinc amalgam, zinc, or tin in a hydroxylic solvent or in the presence of an aqueous mineral or organic acid such as formic acid, acetic acid, or hydrochloric acid.

The oxime of structure 3 can be prepared by any suitable art-known procedure such as nitrosation of the appropriate diketone of the structure 4:

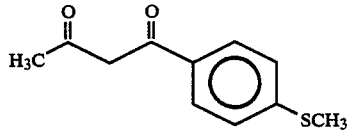

4

Suitable nitrosation reactions are reviewed by O. Tousler in "Organic Reactions" Volume VII, pp. 327-377.

The amount of the active ingredient to be administered can vary widely according to the particular dosage unit employed, the mode of administration, the period of treatment, the age and sex of the patient treated, and the nature and extent of the disorder treated. The total amount of the active ingredient to be administered will generally range from about 1 mg/kg to 100 mg/kg and preferably from 3 mg/kg to 30 mg/kg. A unit dosage may contain from 25 to 525 mg of active ingredient, and can be taken one or more times per day. The active compound of formula 1 can be administered with a pharmaceutical carrier using conventional dosage unit forms either orally, parenterally, or topically.

For oral administration the compound can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compound of this invention can be tableted with conventional tablet bases such as lactose, sucrose, or cornstarch in combination with binders such as acacia, cornstarch, or gelatin, disintegrating agents intended to assist the break-up and dissolution of the tablet following administration such as potato starch, alginic acid, corn starch, or guar gum, lubricants intented to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intented to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compound of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol. A preferred mode of administration is by intraveneous injection or by an intracardiac catheter employing an aqueous solution of the compound of structure 1 with sodium hydroxide, preferably about a 12 N solution of sodium hydroxide.

The active ingredient may also be administered by means of a sustained release system whereby the compound of formula 1 is gradually released at a controlled, uniform rate form an inert or bioerodible carrier by means of diffusion, osmosis, or disintegration of the carrier during the treatment period. Controlled release drug delivery systems may be in the form of a patch or bandage applied to the skin or to the buccal, sublingual, or intranasal membranes, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of the compound of formula 1. The unit dosage of the compound administered by means of a sustained release system will approximate the amount of an effective daily dosage multiplied by the maximum number of days during which the carrier is to remain on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysulphones, polysiloxanes, and polyimides as wells as mixtures and copolymers of these polymers. The compound of formula 1 may be incorporated in the sustained release carrier in a pure form or may be dissolved in any suitable liquid or solid vehicle, including the polymer of which the sustained release carrier is formed.

As used herein the term patient is taken to mean warm blooded animals, for example, birds such as chickens and turkeys, and mammals such as primates including humans, sheep, horses, cattle, pigs, cats, dogs, rats, and mice.

Reperfusion injury is that injury which occurs when molecular oxygen is reintroduced into an ischemic tissue. The ischemia can be caused by any means and in any tissue and includes ischemia to the heart or a portion of the heart resulting from a coronary thrombosis or any other blockage of the blood supply to the heart or a portion of the heart, ischemia surgically induced to the heart of a patient undergoing open-heart or coronary by-pass surgery, the ischemia which occurs to an organ or organ group such as a heart, heart-lung, liver, or kidney to be used in an organ transplant, ischemia occuring during circulatory shock, and ischemia which is caused by blockage of the arteries supplying the brain, i.e. stroke. The compound of structure 1 will ideally be administered to the patient at the time of tissue reperfusion and will continue until such time that reperfusion injury of the type being treated has normally ceased and will be for about 2 to 3 days following substantial reperfusion of the tissue. For example, the compound of structure 1 could conveniently be administered to a patient with a coronary thrombosis concurrently with the administration of a clot dissolving agent such as streptokinase or urokinase. Administration of a compound of structure 1 prior to an ischemia may be indicated in certain instances such as where a patient has substantial risk of heart attack or stroke and would continue until the risk of an ischemic event has substantially disappeared, for example, where the patient has recently suffered a heart attack or stroke, or where the patient is to undergo a surgical procedure requiring a temporary, surgically-induced organ ischemia such as in open heart surgery or coronary by-pass surgery.

The ability of the compound of this invention to reduce reperfusion injury can be demonstrated by its ability reduce myocardial stunning, i.e. the prolonged loss of contractile function in the absence of necrosis following short periods of myocardial ischemia. (See E. Braunwald and R. A. Kloner, *Circ.* 66, 1146–1149 (1982). Stunning has been implicated in a variety of disorders and conditions in which blood circulation has been temporarily cut off from the heart or in which a relatively high concentration of oxygen derived free radicals is known to be present.

In order to measure stunning an anesthetized dog is instrumented to record blood pressure, heart rate electrocardiogram (ECG), cardiac contractile force, and left intraventricular systolic pressure and its derivative. Two crystal sets each with two crystals are implanted in the left myocardium to measure shortening of the myocardial segments between the crystals of each set. One set is placed toward the base and the other toward the apex. The apical crystal set is placed to be within the ischemic area during occlusion of the left anterior descending coronary artery (LAD) at the intermediate point. The basal set of crystals are placed to be in the normal myocardium during ischemia. Following a control period, the LAD is occluded for 15 minutes followed by 3 hours of reperfusion. A short period of occlusion is used to prevent any substantial necrosis. During the period of occlusion, the shortening of the myocardial segment between the apical crystals (ischemic myocardium) decreases and actually shows a lengthening during contraction in control dogs whereas the shortening between the basal crystals (nonischemic myocardium) is maintained. When the occlusion period is ended and reperfusion of the ischemic myocardium has commenced, contractility of the previously ischemic area improves but does not recover during the 3 hour reperfusion period. This disparity in contractility (reported as per cent shortening) between the normal and previously ischemic region is referred to as stunning and is reported below in Table 1. To avoid any possible effect on stunning by the positive inotropic activity of the compound of this invention, the positive inotropic effect of the compound was allowed to dissipate at least 80 per cent prior to occlusion of the LAD.

TABLE 1

PREVENTION OF MYOCARDIAL STUNNING
DURING REPERFUSION FOLLOWING 15 MINUTES
OF ISCHEMIA IN ANESTHETIZED DOGS
(% Myocardial Fiber Shortening ± SE)

| TREATMENT | N | BEFORE LAD OCCLUSION (PRE-) | | DURING LAD OCCLUSION | | DURING REPERFUSION | |
|---|---|---|---|---|---|---|---|
| | | NORMAL AREA | ISCHEMIC AREA | NORMAL AREA | ISCHEMIC AREA | NORMAL AREA | ISCHEMIC AREA |
| Vehicle | 7 | 12.4 ± 2.2 | 15.4 ± 1.3 | 14.4 ± 2.3 | −3.2 ± 1.7[a] | 13.8 ± 2.2 | 5.6 ± 1.7[a,b] |
| Structure 1 Compound | 3 | 14.6 ± 2.3 | 17.2 ± 0.9 | 14.8 ± 3.7 | 2.8 ± 3.1[a] | 13.9 ± 3.2 | 12.1 ± 2.2 |
| Milrinone | 3 | 12.4 ± 0.2 | 16.4 ± 2.4 | 14.2 ± 1.6 | −4.7 ± 4.3[a] | 12.1 ± 1.4 | 3.7 ± 5.9[a,b] |

[a]Significant difference from percent shortening in the normal area.
[b]This disparity in shortening from the normal area indicates stunning.

EXAMPLES

The following examples are intended to illustrate the preparation of the compound of structure 1 and the preparation of various pharmaceutical compositions and are not intended to limit the scope of this invention in any way.

EXAMPLE 1

PREPARATION OF 1,3,DIHYDRO-4-METHYL-5-[4-(METHYLTHIO)-BENZOYL]-2H-IMIDAZOL-2-THIONE

A solution of potassium cyanate (4.0 g, 0.04 mole) in water (10 ml.) was added to a solution of 1-4-[(methylthio)benzoyl]-2-amino-butane-1,3-dione (5.3 g, 0.02 mole) in acetic acid (40 ml.). The mixture was stirred overnight at room temperature during which time the product precipitated from the reaction mixture. The precipitate was collected by filtration and recrystallized from ethanol/methanol to give the title compound, m.p. 295° C.

EXAMPLE 2

PREPARATION OF A TABLET FORMULATION

Tables can be prepared each having the following composition.

| INGREDIENT | QUANTITY (mg) |
|---|---|
| 1,3-Dihydro-4-methyl-5-[4-(methylthio)benzoyl]-2H—imidazol-2-thione | 100 |
| Cornstarch | 15 |
| Lactose | 33.5 |
| Magnesium Stearate | 1.5 |

EXAMPLE 3

PREPARATION OF A CAPSULE FORMULATION

Capsules can be prepared each having the following composition.

| INGREDIENT | QUANTITY (mg) |
|---|---|
| 1,3-Dihydro-4-methyl-5-[4-(methylthio)benzoyl]-2H—imidazol-2-thione | 400 |
| Talc | 40 |
| Sodium Carboxymethylcellulose | 40 |
| Starch | 120 |

EXAMPLE 4

PREPARATION OF A PARENTERAL FORMULATION

A parenteral formulation is prepared, each unit dosage having the following composition.

| INGREDIENT | QUANTITY |
|---|---|
| 1,3-Dihydro-4-methyl-5-[4-(methylthio)benzoyl]-2H—imidazol-2-thione | 1.0 g |
| Polyoxyethylene Sorbitan Monooleate | 2.0 g |
| Sodium Chloride | 0.128 g |
| Water for Injection qs ad | 20.0 ml |

We claim:
1. The compound 1,3-dihydro-4-methyl-5-[4-(methylthio)benzoyl]-2H-imidazol-2-thione or a pharmaceutically acceptable salt thereof.

* * * * *